US00PP23600P2

(12) United States Plant Patent
Bowyer

(10) Patent No.: US PP23,600 P2
(45) Date of Patent: May 14, 2013

(54) ***HELICHRYSUM* PLANT NAMED 'EMBER GLOW'**

(50) Latin Name: *Helichrysum×amorginum*
Varietal Denomination: Ember Glow

(76) Inventor: Brenda Marion Bowyer, Chaddesden (GB)

( * ) Notice: Subject to any disclaimer, the term of this patent is extended or adjusted under 35 U.S.C. 154(b) by 137 days.

(21) Appl. No.: 13/134,384

(22) Filed: Jun. 6, 2011

(51) Int. Cl.
*A01H 5/00* (2006.01)

(52) U.S. Cl.
USPC ..... Plt./359

(58) Field of Classification Search ..... Plt./359
See application file for complete search history.

*Primary Examiner* — June Hwu
(74) *Attorney, Agent, or Firm* — C. A. Whealy

(57) ABSTRACT

A new and distinct cultivar of *Helichrysum* plant named 'Ember Glow', characterized by its mounding plant habit; freely branching growth habit, bushy growth form; numerous inflorescences positioned above the foliar plane; red-colored involucral bracts that become light red to orange red with development; and good postproduction longevity and garden performance.

2 Drawing Sheets

Botanical designation: *Helichrysum×amorginum.*
Cultivar denomination: 'EMBER GLOW'.

BACKGROUND OF THE INVENTION

The present invention relates to a new and distinct cultivar of *Helichrysum* plant, botanically known as *Helichrysum× amorginum* and hereinafter referred to by the name 'Ember Glow'.

The new *Helichrysum* plant is a product of a controlled breeding program conducted by the Inventor in Derby, Chaddesden, United Kingdom. The objective of the breeding program is to create new mounding *Helichrysum* plants with unique and attractive inflorescence color.

The new *Helichrysum* plant originated from a cross-pollination in March, 1999 in Derby, Chaddesden, United Kingdom, of *Helichrysum×amorginum* 'Blorub', disclosed in U.S. Plant patent application Ser. No. 11/177,992 (abandoned), as the female, or seed, parent with an unnamed proprietary selection of *Helichrysum×amorginum*, not patented, as the male, or pollen, parent. The new *Helichrysum* plant was discovered and selected by the Inventor as a single flowering plant from within the progeny of the stated cross-pollination in a controlled environment in Derby, Chaddesden, United Kingdom in March, 2000.

Asexual reproduction of the new *Helichrysum* plant by vegetative cuttings in a controlled environment in Derby, Chaddesden, United Kingdom since July, 2000, has shown that the unique features of this new *Helichrysum* plant are stable and reproduced true to type in successive generations.

SUMMARY OF THE INVENTION

Plants of the new *Helichrysum* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Ember Glow'.

These characteristics in combination distinguish 'Ember Glow' as a new and distinct *Helichrysum* plant:

1. Mounding plant habit.
2. Freely branching growth habit, bushy growth form.
3. Numerous inflorescences positioned above the foliar plane.
4. Red-colored involucral bracts that become light red to orange red with development.
5. Good postproduction longevity and garden performance.

Plants of the new *Helichrysum* differ primarily from plants of the female parent, 'Blorub', primarily in involucral bract color as plants of 'Blorub' have red-colored involucral bracts.

Plants of the new *Helichrysum* differ primarily from plants of the male parent selection primarily in involucral bract color as plants of the male parent selection have yellow-colored involucral bracts.

Plants of the new *Helichrysum* can also be compared to plants of the *Helichrysum×amorginum* 'Pink Sapphire', disclosed in U.S. Plant Pat. No. 20,476. In side-by-side comparisons conducted in Derby, Chaddesden, United Kingdom, plants of the new *Helichrysum* differed primarily from plants of 'Pink Sapphire' in involucral bract color as plants of 'Pink Sapphire' had pink-colored involucral bracts.

BRIEF DESCRIPTION OF THE PHOTOGRAPHS

The accompanying colored photographs illustrate the overall appearance of the new *Helichrysum* plant showing the colors as true as it is reasonably possible to obtain in colored reproductions of this type. Colors in the photographs may differ slightly from the color values cited in the detailed botanical description which accurately describe the colors of the new *Helichrysum* plant.

The photograph on the first sheet comprises a top perspective view of typical flowering plants of 'Ember Glow' grown in an outdoor nursery.

The photograph on the second sheet is a close-up view of a typical inflorescence of 'Ember Glow'.

DETAILED BOTANICAL DESCRIPTION

The aforementioned photographs and following observations, measurements and values describe plants grown during the summer in ground beds in an outdoor nursery in Bressingham, Norfolk, United Kingdom and under commercial practices. During the production of the plants, day temperatures ranged from 8° C. to 30° C. and night temperatures ranged from −3° C. to 15° C. Plants were one year old when the photographs and description were taken. In the following description, color references are made to The Royal Horticultural Society Colour Chart, 2001 Edition, except where general terms of ordinary dictionary significance are used.

Botanical classification: *Helichrysum×amorginum* 'Ember Glow'.

Parentage:

*Female, or seed, parent.*—*Helichrysum×amorginum* 'Blorub', disclosed in U.S. Plant patent application Ser. No. 11/177,992 (abandoned).

*Male, or pollen, parent.*—Unnamed selection of *Helichrysum×amorginum*, not patented.

Propagation:

*Type.*—By vegetative cuttings.

*Time to initiate roots.*—About 15 days at temperatures of 18° C. to 21° C.

*Time to produce a rooted young plant.*—About 70 days at temperatures of 18° C. to 25° C.

*Root description.*—Thin, fibrous; color, close to 161B.

*Rooting habit.*—Freely branching; dense.

Plant description:

*Plant form and growth habit.*—Mounding plant habit; moderately vigorous growth habit; freely branching growth habit and bushy plant form.

*Plant height.*—About 35 cm.

*Plant diameter or spread.*—About 40 cm.

*Lateral branches.*—Arrangement: Many lateral branches arising in a basal rosette. Length: About 20 cm to 26 cm. Diameter: About 4 mm. Internode length: About 1 cm. Strength: Strong. Aspect: Upright to pendulous. Texture: Densely pubescent, pannose. Color: Close to 189B to 189C.

Foliage description:

*Arrangement.*—Alternate, simple; sessile.

*Length.*—About 6 cm to 8 cm.

*Width.*—About 1.5 cm.

*Shape.*—Lanceolate.

*Apex.*—Obtuse.

*Base.*—Acuminate.

*Margin.*—Entire.

*Texture, upper and lower surfaces.*—Pubescent.

*Venation pattern.*—Pinnate.

*Color.*—Developing and fully expanded leaves, upper surface: Close to 189B; venation, close to 189B. Developing and fully expanded leaves, lower surface: Close to 189C; venation, close to 189C.

Inflorescence description:

*Appearance and flowering habit.*—Composite inflorescence form; inflorescences arranged in terminal compound umbels; involucral bracts arranged acropetally in numerous whorls on the receptacle; inflorescences borne above the foliar plane; uniform and freely flowering habit; inflorescences face mostly upright.

*Fragrance.*—None detected.

*Flowering season.*—Plants flower from spring through autumn in the United Kingdom; flowering continuous during this period.

*Inflorescence longevity.*—Inflorescences are long-lasting and can be cut and dried without color fading; inflorescences persistent.

*Inflorescence bud.*—Height: About 1 cm. Diameter: About 5 mm. Shape: Orbicular. Color: Close to 46A.

*Inflorescence size.*—Umbel diameter: About 5 cm. Umbel height: About 4 cm. Single inflorescence diameter: About 1 cm. Single inflorescence height: About 1 cm. Diameter of disc: About 0.5 mm. Receptacle diameter: About 1 mm. Receptacle height: About 5 mm. Receptacle color: Close to 189D.

*Involucral bracts.*—Quantity per inflorescence: Typically about 100 in numerous whorls. Length: About 4 mm. Width: About 1 mm. Shape: Obovate. Apex: Obtuse. Base: Attenuate. Margin: Entire. Texture, upper and lower surfaces: Scarious. Color: When opening, upper surface: Close to 47A; towards the base, close to 47B; color becoming closer to 41A with development. When opening, lower surface: Close to 47B; color becoming closer to 33C with development. Fully opened, upper surface: Close to 31A; towards the base, close to 29B. Fully opened, lower surface: Close to 29C.

*Ray florets.*—Development of ray florets has not been observed on plants of the new *Helichrysum.*

*Disc florets.*—Arrangement: Massed at center of receptacle; upright; numerous disc florets develop per inflorescence. Shape: Tubular, elongated. Apex: Acute. Length: About 1 mm. Width: Less than 1 mm. Texture: Smooth, glabrous. Color, immature: Close to 150C. Color, mature: Apex, close to 2A; mid-section, close to 150A; base, close to 150C. Quantity per inflorescence: Numerous.

*Phyllaries.*—Length: About 2 mm. Width: About 2 mm. Shape: Obovate. Apex: Obtuse. Base: Attenuate. Margin: Entire. Texture, upper and lower surfaces: Pubescent. Color, upper and lower surfaces: Close to 189D.

*Peduncles.*—Length: About 1 cm. Diameter: About 1 mm. Strength: Strong. Texture: Pubescent. Color: Close to 189D.

*Pedicels.*—Length: About 5 mm. Diameter: About 1 mm. Strength: Strong. Texture: Pubescent. Color: Close to 189D.

*Reproductive organs.*—Present on disc florets only. Androecium: Quantity per floret: Typically five. Filament length: About 2 mm. Filament diameter: About 0.05 mm. Filament color: Close to 31A. Anther length: About 1 mm. Anther diameter: About 0.05 mm. Anther shape: Cylindrical. Anther color: Close to 31A. Pollen amount: Sparse. Pollen color: Close to 23C. Gynoecium: Quantity per floret: One. Pistil length: About 2 mm. Style length: About 1.5 mm. Style color: Close to 149C. Stigma length: About 0.05 mm. Stigma color: Close to 23A. Ovary color: Close to 149C.

*Seeds.*—Size: Dust-like. Color: Light brown.

Disease/pest resistance: Plants of the new *Helichrysum* have been observed to be tolerant to Mildew pathogens. Plants of the new *Helichrysum* have not been observed to be resistant to pests and other pathogens common to *Helichrysum* plants.

Garden performance: Plants of the new *Helichrysum* have been observed to have good garden performance and tolerate rain, wind and temperatures ranging from about −8° C. to about 30° C.

It is claimed:

1. A new and distinct *Helichrysum* plant named 'Ember Glow' as illustrated and described.

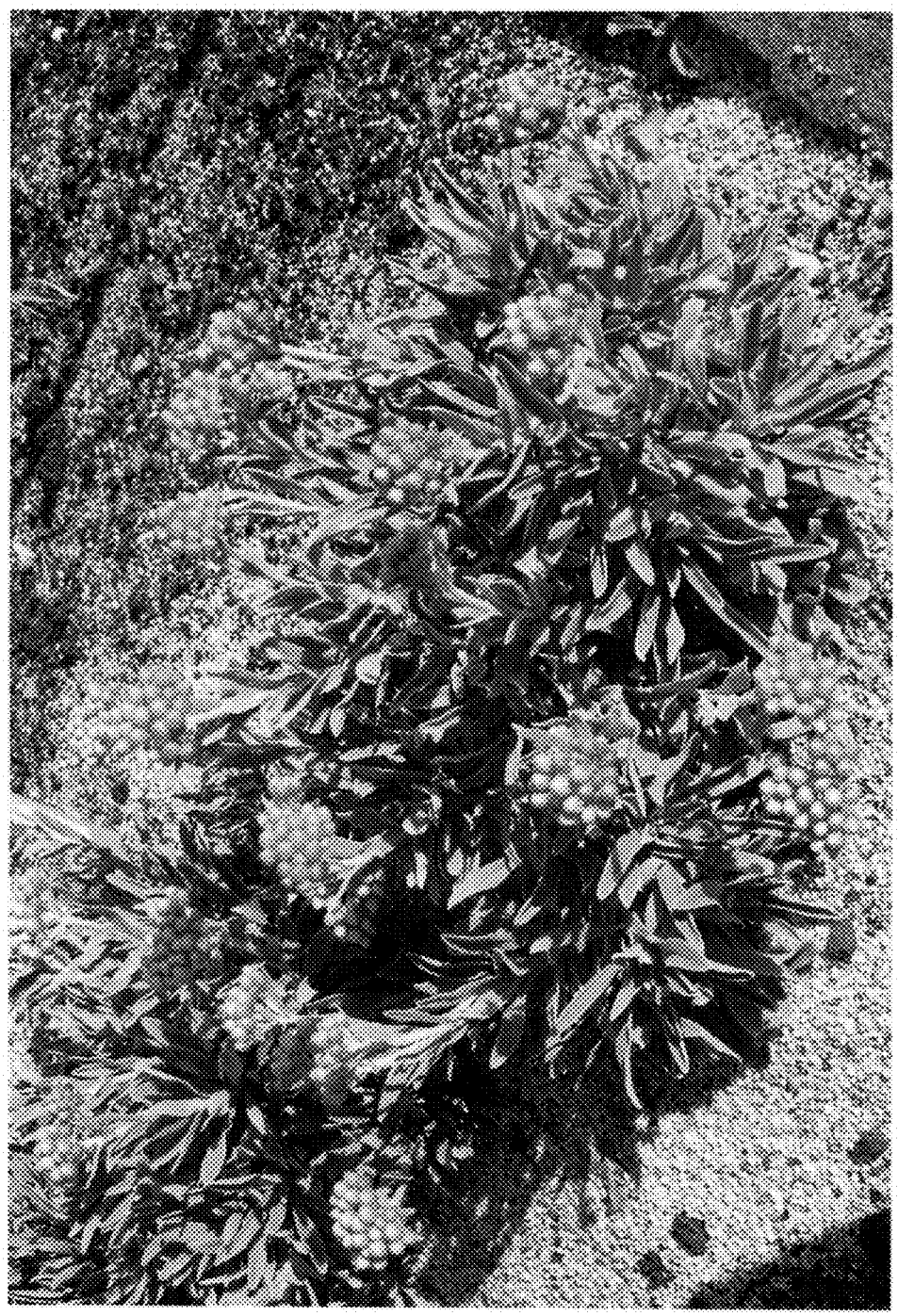

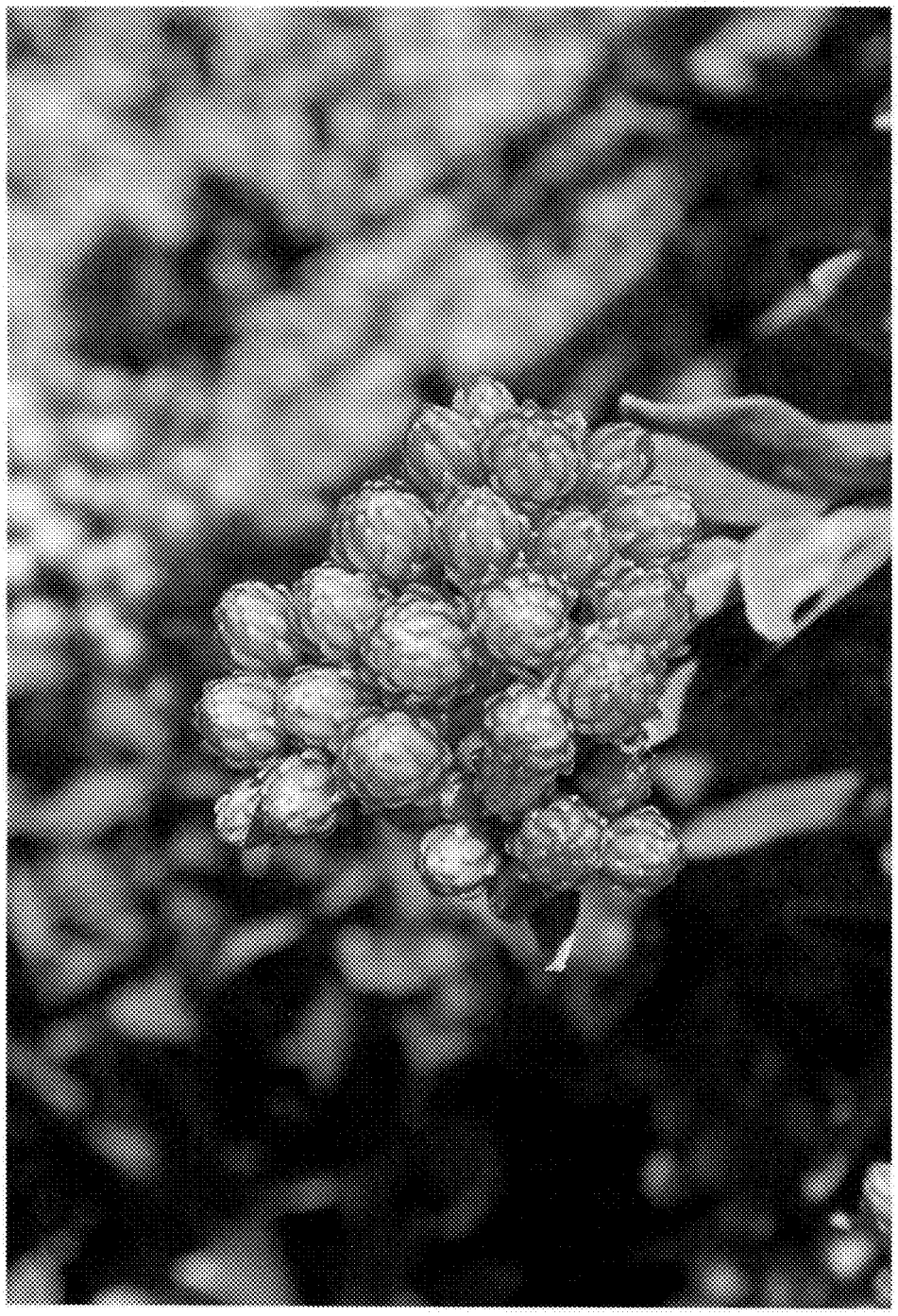

* * * * *